US011129862B2

(12) United States Patent
Bai et al.

(10) Patent No.: US 11,129,862 B2
(45) Date of Patent: Sep. 28, 2021

(54) OPHTHALMIC COMPOSITIONS

(71) Applicant: Johnson & Johnson Consumer Inc., Skillman, NJ (US)

(72) Inventors: Mingqi Bai, Jacksonville, FL (US); Kenneth T. Holeva, Ponte Vedra Beach, FL (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 263 days.

(21) Appl. No.: 16/113,073

(22) Filed: Aug. 27, 2018

(65) Prior Publication Data

US 2019/0060385 A1  Feb. 28, 2019

Related U.S. Application Data

(60) Provisional application No. 62/552,066, filed on Aug. 30, 2017.

(51) Int. Cl.
| | |
|---|---|
| *A61K 36/48* | (2006.01) |
| *A61K 9/08* | (2006.01) |
| *A61K 31/728* | (2006.01) |
| *A61P 27/04* | (2006.01) |
| *A61K 31/717* | (2006.01) |
| *A61K 9/00* | (2006.01) |
| *A61K 47/38* | (2006.01) |
| *A61K 31/715* | (2006.01) |
| *A61K 47/36* | (2006.01) |

(52) U.S. Cl.
CPC ............ *A61K 36/48* (2013.01); *A61K 9/0048* (2013.01); *A61K 9/08* (2013.01); *A61K 31/715* (2013.01); *A61K 31/717* (2013.01); *A61K 31/728* (2013.01); *A61K 47/36* (2013.01); *A61K 47/38* (2013.01); *A61P 27/04* (2018.01)

(58) Field of Classification Search
None
See application file for complete search history.

(56) References Cited

U.S. PATENT DOCUMENTS

| | | |
|---|---|---|
| 3,396,081 A | 8/1968 | Billek |
| 3,862,003 A | 1/1975 | Okuyama et al. |
| 4,141,973 A | 2/1979 | Balazs |
| 4,328,803 A | 5/1982 | Pape |
| 4,517,296 A | 5/1985 | Sakakibara et al. |
| 4,851,521 A | 7/1989 | della Valle et al. |
| 4,965,353 A | 10/1990 | della Valle et al. |
| 5,202,431 A | 4/1993 | della Valle et al. |
| 5,316,926 A | 5/1994 | Brown et al. |
| 6,056,950 A * | 5/2000 | Saettone ............... A61K 47/36 424/78.04 |
| 6,090,596 A | 7/2000 | Stahl |
| 6,339,074 B1 | 1/2002 | Cialdi et al. |
| 8,455,462 B2 * | 6/2013 | Del Prete ............ A61K 31/715 514/54 |
| 2006/0094643 A1 | 5/2006 | Svirkin et al. |
| 2008/0138310 A1 | 6/2008 | Ketelson et al. |
| 2008/0273171 A1 | 11/2008 | Huth et al. |
| 2013/0005805 A1 | 1/2013 | Gallois-Bernos et al. |
| 2014/0364400 A1 | 12/2014 | Gallois_Bernos |
| 2017/0196805 A1 * | 7/2017 | Si ..................... A61K 9/0048 |
| 2017/0252451 A1 * | 9/2017 | Bai .................... A61K 9/0048 |
| 2020/0030394 A1 * | 1/2020 | Li ........................ A61P 27/00 |

FOREIGN PATENT DOCUMENTS

| | | |
|---|---|---|
| EP | 2011486 A1 | 1/2009 |
| JP | 2000/060487 | 2/2000 |
| WO | 2009008005 A1 | 1/2009 |
| WO | 2009044423 A1 | 4/2009 |
| WO | 2012087326 A1 | 6/2012 |
| WO | 2012136369 A1 | 10/2012 |
| WO | 2015168523 A1 | 11/2015 |
| WO | 2015193677 A1 | 12/2015 |

OTHER PUBLICATIONS

Di Colo G. et al. Selected Polysaccharides at Comparison for Their Mucoadhesiveness and Effect on Precorneal Residence of Different Drugs in the Rabbit Model. Drug Development and Industrial Pharmacy 35(8)941-949, Aug. 2009 (Year: 2009).*
Wilson, C. Topical Drug Delivery in the Eye. Experimental Eye Research 78(3)737-743, Mar. 2004. (Year: 2004).*
Burgalassi S, et al. Devleopment of a Simple Dry Eye Model in the Albino Rabbit and Evaluation of Some Tear Substitutes. Ophthalmic Research 31(3)229-235, May/Jun. 1999. (Year: 1999).*
Barbarino S. et al. The Effect of Artificial Tear Combining Hyaluronic Acid and Tamarind Seeds Polysaccharide . . . European J of Ophthalmology 24(2)173-178, 2014. (Year: 2014).*
Asheim et al, Intra-Articular Treatment of Arthritis in Race-Horses with Sodium Hyaluronate, Acta Vet. Scand., vol. 17, pp. 379-394 (1976).
Darmon, Retinoic acid in skin and epithelia, Seminars in Developmental Biology, vol. 2, (1991), pp. 219-223.
Gorodeski et al., Regulation by retinoids of P2Y2 nucleotide receptor mRNA in human uterine cervical cells, American Physiological Society, vol. 275, pp. 758-765 (1998).
Gupta et al, Tamarind Kernel Gum: An Upcoming Natural Polysaccharide, Sys Rev Pharm, vol. 1, Issue 1, Jan.-Jun. 2010, pp. 50-54.
Kim et al., A Comparison of Vitamin A and Cyclosporine A 0.05% Eye Drops for Treatment of Dry Eye Syndrome, American Journal of Ophthalmology, vol. 147, No. 2, pp. 206-213.e3 (2009).
Kligman, Topical Tretinoin: Indications, Safety, and Effectiveness, CUTIS, vol. 39, pp. 486-488 (Jun. 1987).
Kobayashi et al., Effect of Retinol Palmitate as a Treatment for Dry Eye: A Cytological Evaluation, Ophthalmologica, vol. 211, pp. 358-361 (1997).

(Continued)

*Primary Examiner* — Ralph J Gitomer

(57) ABSTRACT

The present invention relates to compositions providing improved substantivity, comfort and/or feel to the eye upon application. The present invention further relates to compositions comprising a cellulose derivative in combination with tamarind seed extract and hyaluronic acid in ratios that mimic the physical properties of human tears on the eye.

11 Claims, No Drawings

(56) References Cited

OTHER PUBLICATIONS

Lang et al., Investigations on the Solution Architectyure of Carboxylated Tamarind Seed Polysaccharide by Static and Dynamic Light Scattering, Macromolecules, vol. 26, pp. 3992-3998, (1993).
PCT International Search Report, dated Nov. 27, 2018, for PCT Int'l Appln. No. PCT/IB2018/056592.
Selek et al., Evalutation of retinoic acid ophthalmic emulsion in dry eye, European Journal of Ophthalmology, vol. 10, No. 2, pp. 121-127 (2000).

* cited by examiner

OPHTHALMIC COMPOSITIONS

RELATED APPLICATIONS

This application claims the benefit of the earlier filing date of U.S. Provisional Patent Application No. 62/552,066, filed Aug. 30, 2017, the entirety of which application is hereby incorporated by reference herein as if fully set forth herein.

FIELD OF THE INVENTION

The present invention relates to compositions providing improved substantivity, comfort and/or feel to the eye upon application. The present invention further relates to compositions comprising a cellulose derivative in combination with tamarind seed extract and hyaluronic acid in ratios that mimic the physical properties of human tears on the eye.

BACKGROUND OF THE INVENTION

Ophthalmic solutions are sterile solutions, free or substantially free from foreign particles and/or microorganisms, for instillation into the eye. For certain applications, ophthalmic solutions do not contain medications and are used as lubricating, tear-replacing, and eye wash solutions, and/or packing solutions, multipurpose, and other solutions for contact lenses. Ophthalmic solutions can also contain pharmacologically active ingredients and be used to treat such environment related eye conditions as dry eye, allergies, eye infections such as pink eye, minor eye irritations or conjunctivitis, or structurally related eye conditions such as glaucoma. They can also be used diagnostically by opticians as mydriatic compositions to dilate the pupils of patients during eye examinations.

To avoid or reduce such negative effects of ophthalmic compositions on the eye such as the feel of "dragging" (of such compositions) across the eye upon blinking, blurriness upon application to the eye and discomfort (of such compositions) due to unpleasant film formation of the eye, it is critical to provide ophthalmic compositions which mimic (i.e., physical properties which are the same as or similar to) the physical properties of tears on the eye.

There is, therefore, a need for compositions useful as ophthalmic solutions, which upon application to the eye, provide improved eye feel by exhibiting the same or similar physical properties as human tears with respect to the surfaces of the eye and eye lid. This composition will aid in increased tear stability, a reduction in moisture loss from the tears, and protection of the ocular surface

SUMMARY OF THE INVENTION

The present invention relates to a composition, comprising:
  a polymer mixture comprising
    i. a cellulose derivative;
    ii a tamarind seed extract; and
    iii hyaluronic acid;
  optionally, an oil component;
  optionally, a surfactant; and
  optionally, an aqueous component
wherein the cellulose derivative, tamarind seed extract and hyaluronic acid are combined at a ratio of: 1 to 10 parts cellulose derivative: 1 to 4 parts tamarind seed extract: 1 to 2 parts hyaluronic acid, to form the polymer mixture.

DETAILED DESCRIPTION OF THE INVENTION

The compositions and methods of the present invention can comprise, consist of, or consist essentially of the steps, essential elements and limitations of the invention described herein, as well any of the additional or optional ingredients, components, or limitations described herein. The term "comprising" (and its grammatical variations) as used herein is used in the inclusive sense of "having" or "including" and not in the exclusive sense of "consisting only of." The terms "a" and "the" as used herein are understood to encompass the plural as well as the singular.

Unless otherwise indicated, all documents cited are, in relevant part, incorporated herein by reference; the citation of any document is not to be construed as an admission that it is prior art with response to the present invention. Furthermore, all documents incorporated herein by reference or incorporated herein by reference in their entirety are only incorporated herein to the extent that they are not inconsistent with this specification.

In certain embodiments, the present invention as disclosed herein may be practiced in the absence of any compound or element (or group of compounds or elements) which is not specifically disclosed herein.

Cellulose Derivatives

The compositions of the present invention comprise a cellulose derivative. Suitable cellulose derivatives include, but are not limited to, hydroxyalkyl cellulose polymers and alkyl hydroxyalkyl cellulose polymers such as hydroxyethyl cellulose, hydroxypropyl cellulose, cetyl hydroxyethyl cellulose and mixtures thereof; methyl cellulose; methyl cellulose derivatives such as carboxymethyl cellulose (crosscarmellose), hydroxymethylcellulose, hydroxymethylcellulose and mixtures thereof;

hydroxymethycellulose derivatives such as hydroxypropyl methylcellulose (HPMC or hypromellose) and hydroxybutyl methyl cellulose and mixtures thereof; and mixtures of any of the above cellulose derivatives, In certain embodiments the cellulose derivative is hydroxypropyl methylcellulose.

In certain embodiments, the cellulose derivative used herein is a low viscosity grade cellulose derivative. By the term "low viscosity grade" is meant a cellulose derivative having a viscosity of from about 1-100 cps (at 2% aqueous at 20° C.). Such low viscosity grades are indicated by notations like "E3" as in the case of Hypromellose E3 2910 or Hypromellose E3 Premium 2910, which compounds typically have a viscosity of from about 1-10 cps (at 2% aqueous at 20° C.). A low viscosity grade of carboxmethylcellulose (CMC) is typically indicated by notations like "L", as in the case of Sodium CMC 7L2P, which compounds typically have a viscosity of from about 25-50 cps (at 2% aqueous at 20° C.).

The cellulose derivative can be present in the composition of the present invention at concentrations of from about 0.1% w/v to about 2.5% w/v, optionally from about 0.2% w/v to about 1.0% w/v, or optionally from about 0.2% w/v to about 0.5% w/v of the total composition.

Tamarind Seed Extract

The compositions of the present invention also comprise a tamarind seed extract. Tamarind tree is widespread in India, Africa and in the South East Asia. In Middle Eastern countries, tamarind juice from the tamarind fruit can be a drink prepared by infusing dried tamarind pulp. Tamarind can also be useful for the preservation of food products and as a sauce in recipes.

The tamarind seed finds various applications, once ground to the powder form (known as "tamarind gum" or "tamarind kernel powder"). Commercially available tamarind kernel powder can be employed as thickener and a sizing agent in textile and paper industries; and as thickening, gelling, stabilizing and binding agent in food and pharmaceutical industries.

General properties, chemical composition and chemical structure of tamarind kernel powder and of tamarind seed polysaccharide can be found in: Gupta V, Puri R, Gupta S, Jain S, Rao G K.; Tamarind kernel gum: an upcoming natural polysaccharide. Syst Rev Pharm; 2010; 1:50-4.

Tamarind seed polysaccharide or extract (TSP) is a nonionic, neutral, branched polysaccharide comprising a cellulose-like backbone substituted by xylose (a 1→6) and galacto (β1→2)xylose (a 1→6) substituents (Lang P. et al., Macro molecules, 1993, 26, 3992-3998).

As is known by those skilled in the art, the tamarind seed polysaccharide is extracted from tamarind seeds has been described as a viscosity enhancer showing mucomimetic, mucoadhesive, and bioadhesive activities. Several features make TSP an attractive candidate as a vehicle for ophthalmic medicaments, since it (i) is completely devoid of ocular toxicity; (ii) is on the market as a tear fluid substitute because of its activity in preventing alterations of the corneal surface known as keratoconjunctivitis sicca; and (iii) increases the corneal-wound healing rate when used in concentrations between 0.25% and 1%.

The tamarind seed extract can be present in the composition of the present invention at concentrations of from about 0.05% w/v to about 2% w/v, optionally from about 0.1% w/v to about 1% w/v, or optionally from about 0.2% w/v to about 0.5% w/v of the total composition.

Hyaluronic Acid

Hyaluronic acid is used in literature to designate an acidic polysaccharide with various molecular weights constituted by residues of D-glucuronic acid and N-acetyl-D-glucosamine, which naturally occur in cellular surfaces, in the basic extracellular substances of the connective tissues of vertebrates, in the synovial fluid of joints, in the vitreous humor of the eye, in the tissue of the human umbilical cord and in cocks' combs.

As a therapeutic agent, hyaluronic acid and its salts have been used especially in therapy for arthropathies, such as in veterinary medicine for the cure of arthritis in horses [Acta Vet. Scand. 167, 379 (1976)]. As an auxiliary and substitutional therapeutic agent for natural tissues and organs, hyaluronic acid and its molecular fractions and their salts have been used in ophthalmic surgery (see for example Balazs et al., Modern Problems in Ophthalmology, Vol. 10, 1970, p. 3—E. B. Strieff, S. Karger eds., Basel; Viscosurgery and the Use of Sodium Hyaluronate During Intraocular Lens Implantation, Paper presented at the International Congress and First Film Festival on Intraocular Implantation, Cannes, 1979; U.S. Pat. No. 4,328,803 with a summary of the literature on the uses of HY in ophthalmology; and U.S. Pat. No. 4,141,973.

In certain embodiments, the HA has a molecular weight between about 500,000 daltons and about 4,000,000 daltons, or, optionally, between about 1,000,000 daltons and about 2,000,000 daltons, or, optionally, between about 1,200,000 daltons and about 1,800,000 daltons. Certain embodiments of the present invention contain between about 0.1% and about 0.5% HA, or, optionally, between about 0.2% and about 0.4% HA, or, optionally, about 0.2% HA. More detailed discussions of HA can be found in U.S. Patent Publication 20060094643; and U.S. Pat. Nos. 3,396,081; 3,862,003; 4,141,973; 4,517,296; 4,851,521; 4,965,353; 5,202,431; 5,316,926; 6,090,596; and 6,339,074, each of which patents are herein incorporated by reference in its entirety.

The hyaluronic acid can be present in the composition of the present invention at concentrations of from about 0.05% w/v to about 1% w/v, optionally from about 0.075% w/v to about 0.5% w/v, or optionally from about 0.1% w/v to about 0.4% w/v of the total composition.

In one embodiment, the cellulose derivative is combined with tamarind seed extract and hyaluronic acid to form a polymer mixture for use in improving the physical properties of ophthalmic compositions to mimic the physical properties of tears, namely so as to improve such physical properties of the ophthalmic composition as: surface tension, moisture retention, shear thinning, elastic modulus and phase angle.

Surface Tension Property

The typical volume of a single drop of an ophthalmic composition (about 40-50 microliters) generally exceeds the total tear volume that is on the ocular surface prior to application. This surge in volume produced by an eye drop may exceed the tear "holding capacity" of an eye resulting in an excess of composition which spills over the lid or exits at the nasal or temporal canthi. Human tear fluid as secreted has a surface tension of about 40 dynes/cm which is lower than water (about 70 dynes/cm), making the tear fluid able to wet the ocular surface effectively. In addition, this low surface tension allows tears to wet the periocular skin effectively which leads to visible drainage of the tears, or tearing, away from the ocular surface onto the skin.

In certain embodiments, the cellulose derivative, tamarind seed extract and hyaluronic acid polymer mixture is incorporated such that the surface tension of the composition ranges from about 40.8 dynes/cm to 51.9 dynes/cm, optionally from about 42 dynes/cm to about 48 dynes/cm, or optionally from about 44 dynes/cm to about 46 dynes/cm. The surface tension can be measured by utilizing the pendant drop method of a Rame-Hart contact angle goniometer (Model 100-00 Series) and a micro-syringe (with a 22 gauge needle) and with DROPimage Advanced software (ver. 2.7) as each is supplied by Rame-Hart Instrument Co., Netcong, N.J. The DROPimage Advanced software captures and analyzes the drop dimensions and profile characteristics in order to accurately calculate the surface tension of a liquid utilizing a built-in calculation based on the Young La-Place equation.

The Rame-Hart—DROPimage Advanced Software Pendant Drop Method

Test Equipment:
Rame-Hart Model 100-00 Series Contact Angle Goniometer
Stocker and Yale Image Lite (model number 20, supplied by Stocker and Yale, Inc.)
Rame-Hart Imaging System U1 Series Video Camera
DROPimage Advanced 2.7 Software
Microsyringe with 22 gauge needle (supplied by Gilmont)

Procedure:
The procedural steps of the Rame-Hart—DROPimage Advanced software Pendant Drop Method are as follows (for performance in a manner consistent with protocol provided with Rame-Hart goniometer and DROPimage software):

a.) the test samples are drawn into the provided microsyringes having the needles;
b.) the Dropimage software is accessed and program opened (to display live video captured by the goniometer's digital video camera); the image light is switched to the "on" position; and the video camera is focused to ensure needle of syringe containing sample can be seen at top of live video;
c.) from the software programs file menu, an experiment is selected for performance using the "Surface Tension-Pendant Drop";
d.) Phase Data for the Experiment is entered:
  i. Droplet Phase input: Water;
  ii. External Phase input: Air, and
  iii. Solid Phase: Steel;
e.) Experiment Timing Data is entered: Total Number of Measurements: 10; Time Interval for each measurement: 1 second;
f.) a pendant drop of the test sample is hung from needle of the micro-syringe by slowly turning barrel of the micro-syringe clockwise;
g.) the Stocker and Yale Image Lite is used to improve drop clarity and focus (measurements should be performed in dark room with minimal vibrations);
h.) when drop clarity and focus has been achieved (i.e., the outline of the drop is dark and crisp), the software program is signaled to run the experiment;
i.) a picture will be taken of the drop and will appear to the left of the screen;
j.) the cross-hairs over laying the picture are moved to capture the entire drop from its top shoulders without including needle and the software program is signaled to to take measurements and a picture of the drop hanging from the needle at 0.1 second intervals from 0 to 1 second as the video camera rolls for 1 second;
k.) a report will be generated, indicating the "Gamma" (i.e., surface tension) of the drop; the mean "Gamma" and the standard deviation of the measurement.

Moisture Retention Property

Moisture retention rate refers to the rate at which moisture is lost from a composition over time, at a given temperature and relative humidity (RH), after application the composition to the eye as measured by the Dynamic Vapor Sorption (DVS) Intrinsic-1 serial number P14F0068 equipped with DVS-Intrinsic Control Software (ver. 1.0.5.1). DVS Intrinsic Control software utilizes proprietary technology to precisely weigh the mass of a fixed quantity of a composition while strictly controlling steps of time, start and finish relative humidity, and start and finish temperature as selected. Although the system is typically used for sorption and desorption curves by inserting isotherm steps at increasing or decreasing humidity, the system is used for purposes of this application to compare water loss of compositions by subjecting each composition to a fixed temperature and relative humidity for a period of time and comparing weight or water loss.

In certain embodiments, the cellulose derivative, tamarind seed extract and hyaluronic acid polymer mixture is incorporated such that the rate of moisture loss for the composition is less than 1 mg/3 minutes at 37° C. and 70% relative humidity.

The DVS Intrinsic Measurement System and DVS-Intrinsic Control Software Method

Test Equipment:
    Dynamic Vapor Sorption Intrinsic-1 serial number P14F0068 instrument supplied by Dynamic Vapor Sorption Measuring Systems, LTD
    $CO_2$ gas source
    DVS Intrinsic Control Software version 1.0.5.1, including the SMS DVS Std Macros add-on program, supplied by Dynamic Vapor Sorption Measuring Systems, LTD
    Loading pans for DVS Intrinsic-1 serial number P14F0068
    Mettler Toledo Analytical balance (Model XS205DU, supplied by Mettler Toledo)
  Procedure:
  The procedural steps of the DVS Intrinsic Measurement System and DVS-Intrinsic Control Software Method are as follows (for performance in a manner consistent with any protocol information provided with the DVS Intrinsic Measurement System and DVS-Intrinsic Control Software System):
    a.) the DVS-Intrinsic Control Software is accessed and program opened;
    b.) from the software program's file menu, an experiment method is created using the "Insert Isotherm Steps" method;
    c.) the following parameters are entered:
      i. a single input time of 800 minutes,
      ii. start humidity of 70% RH,
      iii. stop humidity of 70% RH,
      iv. start temperature of 37° C., and
      v. stop temperature of 37° C.;
    d.) the software program is signaled to store the method;
    e.) the method is then loaded, and the target temperature of 37° C. and 70% RH is verified using the "Instrument Data" tab displayed by the software program.
    f.) test sample data is loaded in the software program;
    g.) tare balance a clean weighing pan by placing the pan on the guide wires in the system chamber using tweezers and close the chamber tightly;
    h.) allow time for the instrument to equilibrate at 37° C. and 70% RH;
    i.) once the pan is tared, three green lights will appear indicating completion of tare process.
    j.) the software program is immediately signaled to finish tare process, open the chamber and quickly remove the loading pan from its position hanging on the guide wires;
    k.) immediately weigh 140 mg of test sample in the tared pan;
    l.) place the pan containing test sample back into the chamber and close chamber tightly;
    m.) when the software program displays the mass reading of 140 mg, the software program is signaled to run the method;
    n.) once the method is run on all desired test samples, the data is analyzed and compared by a macro add-in program called SMS DVS Std Macros. The DVS Analysis Suite runs from within Microsoft Excel to provide an environment for plotting the data with the export data function exporting the DVS data into an excel spreadsheet.

Shear Thinning Property

Shear thinning describes the property of non-Newtonian fluids which have decreased viscosity when subjected to shear strain. As used herein, the "shear-thinning" property of the compositions of the present invention refers to the rheologic property of the compositions such that the compositions upon application of a shear stress (e.g., from pumping, dropping or pouring, dispensing, during manufacture or distribution/application, of the compositions) changes viscosity and becomes less thick and flows more like water. In certain embodiments, the cellulose derivative, tamarind seed extract and hyaluronic acid are incorporated such that compositions of the present invention have a viscosity of from about 30 to 100, optionally from about 50 to 80 centipoise (cps) at zero shear (or rest) are capable of being instilled and remain substantive to the eye. In certain embodiments, the cellulose derivative, tamarind seed extract and hyaluronic acid polymer mixture is incorporated such that the compositions have a viscosity of less than 30 cps at the shear rate of blinking (1/100 sec.); such lower viscosity upon blinking prevents or reduces the dragging feeling of a thick drop (i.e., drop with viscosity of 30 to 100 cps as mentioned above) between the eye and eyelid. The polymer mixture would be preferred to have a marked shear thinning such that the viscosity at rest of 30 to 100 cps ideally decreases to the viscosity of tears (4.4 to 8.3 cps) at the shear rate of blinking (1/100 sec.).

To determine directional differences with respect to the extent of shear thinning of polymer compositions at rest (i.e., zero shear) vs. at the shear rate of blinking (i.e. 1/100 sec.), the TA Instruments AR2000 rheometer can be used. to test flow, creep, and oscillation modes. Using the step ramp flow mode of the rheometer, flow behavior over a variety of shear stress and shear rates can be determined by selecting shear rate ranges at a constant temperature. Resulting flow curves can be compared to determine viscosity as a function of shear rate for various compositions. The greater the rate of viscosity drop would indicate material that is more shear thinning (i.e., pseudoplastic) behavior.

AR2000 Flow Test Method:
Test Equipment:
AR2000 rheometer (supplied by TA Instruments)
Thermo Cube Solid State Cooling System (model number 10-300-ICL-IFN-HT-CT
Steel 4 cm flat plate (40 mm) Cone and Plate Geometry, serial number 951103
Procedure:
The procedural steps of the AR2000 Flow Test Method are as follows (for performance in a manner consistent with any protocol information provided with AR2000 rheometer:
  a) the rheometer and cooling system are both switched "on";
  b) the barrier shield from the drive shaft of the rheometer is removed;
  c) the "TA Rheological Advantage" icon displayed by the software program is selected;
  d) the geometry is screwed onto the drive shaft of the rheometer;
  e) the geometry tab is selected from toolbar displayed by the software program and from the dropdown menu "40 mm steel plate geometry (951193)" is chosen as the geometry;
  f) Once the geometry is chosen, "map geometry" is displayed by the software program and the rheometer is allow time to map the geometry.
  g) the instrument tab at the top tool bar as displayed by the software program is selected and "zero gap" tab is selected to zero the gap for this geometry selected in step e) and the geometry is brought closer to the bottom Peltier plate of the AR2000 without letting it touch the plate using the up and down arrows by displayed by the software program.
  h) once gap is zeroed, and the geometry is allowed to rise to 40,000 um in preparation for loading test sample (by selecting the "back off" tab displayed by the software program).
  i) the test sample is loaded such that it covers the entire area below the circumference of the geometry; (Excess air bubbles should be removed from the test sample.)
  j) "Instrument Status" icon displayed by the software program is selected and "Gap" icon displayed by the software program is, then, selected and the gap is adjusted to 1000 um.
  k) the "send" icon displayed by the software program is then selected to lower the geometry onto the test sample.
  l) a conditioning step of one minute, 25° C. is entered, with no pre-shear and, for the flow step, a Ramp type of steady state flow with a start controlled variable of 0 $sec^{-1}$ to an end variable of 200 $sec^{-1}$ is entered;
  m) the experiment is started and the generated data retrieved using the AR2000 Data Analysis program, which transfers the generated viscosity at "blinking" and viscosity "at rest" (i.e., zero shear) data to an Excel program (spreadsheet generator) for comparisons.

A composition can also be characterized by three parameters, elastic modulus G', the viscous modulus G", and its phase angle δ. G' indicates the elasticity of the composition subjected to strain (i.e., its resilience to deformation before it yields). Thus, an elastic composition will be able to absorb the applied energy for a greater range of shear stresses before it breaks down. This is typically indicated by a nearly horizontal G' when plotted as an amplitude sweep curve. The breakdown of thickening matrix is indicated by the point at which G' drops. The shear stress at which this happens is the critical shear stress, and the lower the number, the less resilient the composition. Similarly, the G" is a measure of the viscous nature of the composition, i.e., how much it will flow as a consequence of the applied shear. Some compositions are stiff and resist flow until they break down. Others flow at all shears. High G' and Low G" implies a stiff thick gel, while low G' and high G" implies a runny, highly flowable composition.

The ratio between G' and G" is δ, and gives a measure of the relative "solid" to "fluid" nature of the composition. Phase angles near zero imply a nearly solid-like behavior while those near 90° imply a liquid-like behavior.

In certain embodiments, the cellulose derivative, tamarind seed extract and hyaluronic acid are incorporated to form viscoelastic compositions having:
  i. an elastic modulus G' greater than 0.70 (or about 0.70) Pascals, optionally from about 0.70 (or about 0.70) to about 0.80 (or about 0.80), optionally 0.73 (or about 0.73) to 0.78 (or about 0.78) Pascals, at a strain of from 0 to 0.85; and
  ii. a phase angle δ of from about 40° to about 65°, or optionally from about 50° to about 60°
so as to provide a composition having less fluidity, less deformation, and greater retention in the eye.

The parameters of elastic modulus G', and its phase angle δ can be measured by performing an amplitude sweep of a strain of 0.1 to 10 using the oscillation testing mode of a Bohlin CVOR rheometer and a 60 mm acrylic parallel plate geometry.

Bohlin CVOR Rheometer Visco-Elastic Property Test Method:
Test Equipment:
Bohlin rheometer (Model number C-VOR-150-900; supplied by Malvern Instruments, Inc.)
Neslab Water Bath, Model 100-00
Acrylic 60 mm parallel plate geometry
Procedure:
The procedural steps of the Bohlin CVOR Rheometer Visco-Elastic Property Test Method are as follows (for performance in a manner consistent with any protocol information provided with the Bohlin CVOR Rheometer Test Method):

a) the rheometer and water bath are both switched "on";
b) the lock from the drive shaft of the rheometer is unlocked;
c) the "Bohlin rheometer" icon, oscillation mode, and amplitude sweep are each sequentially selected as they are displayed by the software program;
d) the geometry (i.e., the acrylic 60 mm parallel plate) is screwed onto the drive shaft of the rheometer;
e) a zero gap is selected to ensure that the correct geometry is displayed by the software program. Once the rheometer signals that the gap is zeroed, select the upward arrow displayed by the software program to raise the gap high enough to load the test sample.
f) the test sample is loaded onto the Peltier plate of the rheometer such that it covers the entire area below the circumference of the geometry; (Excess air bubbles should be removed from the test sample.)
g) Select the "Diagram of Experiment" icon displayed by the software program, and then select a "Ramp of Strain" from 0.01 to 10.
h) the experiment is started, generating an amplitude sweep and an accompanying table of data as the experiment progresses to completion;
i) From the curves, the linear viscoelastic regions can be identified and compared. At a stain of 0.85, and the corresponding elastic modulus, G' and phase angle δ are recorded for each of the test samples.

In certain embodiments, the compositions of the present invention exhibit the above rheologic properties when the cellulose derivatives are combined with the tamarind seed extract and hyaluronic acid at a ratio of: 1 to 10, optionally 1 to 5, or optionally 1.5 to 3 parts cellulose derivative: 1 to 4 parts tamarind seed extract: 1 to 2 parts hyaluronic acid, to form the polymer mixture; and, in certain embodiments, where the total concentration of the polymer mixture of cellulose derivative, tamarind seed extract and hyaluronic acid is greater than 0.4% (or about 0.4%) to 0.9% (or about 0.9%), optionally from 0.45% (or about 0.45%) to 0.55% (or about 0.55%), by weight, of the total composition of the present invention. In certain embodiments, the cellulose derivative is hydroxypropylmethyl cellulose.

In certain embodiments, the total concentration of any non-ionic and/or anionic polymers of the composition is from (or greater than) 0.4% (or about 0.4%) to 1.0% (or about 1.0%), by weight, of the total composition of the present invention.

Optional Components
Polyquaternium Compound

In certain embodiments, the compositions of the present invention comprise a polyquaternium compound. Polyquaternium is the International Nomenclature for Cosmetic Ingredients designation for several polycationic polymers that are used in the personal care industry. These polymers have quaternary ammonium centers in the polymer. INCI has approved at least 37 different polymers under the polyquaternium designation. They are cationic molecules. Some have antimicrobial properties, and find particular application in conditioners, shampoo, hair mousse, hair spray, hair dye, contact lens packing solution and contact lens solutions (including eye lubricants, rewetting solutions, rinsing solutions etc.). Different polymers are distinguished by the numerical value that follows the word "polyquaternium". The numbers are assigned in the order in which they are registered rather than because of their chemical structure. Some of the more common quaternary ammonium compounds include those generically referred to in the art as polyquaternium.

In some embodiments, the composition will contain one or more of a polyquaternium compound(s) having a weight average molecular weight of from about 150 to about 15,000 Daltons, optionally from about 200 to about 13,500 Daltons, or optionally from about 250 to about 12,000 Daltons at a level of from about 0.0005% w/v to about 0.1000% w/v, or from about 0.0010% w/v to about 0.0200% w/v, or from about 0.0010% w/v to about 0.0050% w/v of the total composition.

Examples of suitable polyquaternium compounds include, but are not limited to, polyquaternium-1, polyquaternium-10, polyquaternium-42 or mixtures. In an embodiment of the present invention, the polyquaternium compound is polyquaternium-42.

Polyquatemium-1 is also known as ethanol, 2,2',2"-nitrilotris-, polymer with 1,4-dichloro-2-butene and N,N,N', N'-tetramethyl-2-butene-1,4-diamine. Polyquatemium-10 is also known as quaternized hydroxyethyl cellulose. Polyquatemium-42 is also known as poly[oxyethylene(dimethylimino)ethylene (dimethylimino)ethylene dichloride].

Borate

In certain embodiments, the compositions of the present invention comprise a borate. As used herein, the term "borate" shall refer to boric acid, salts of boric acid and other pharmaceutically acceptable borates, or combinations thereof. Suitable borates include, but are not limited to, boric acid; alkaline metal salts such as sodium borate, potassium borate; alkaline earth metal salts such as calcium borate, magnesium borate; transition metal salts such as manganese borate; and mixtures thereof.

The borate compound can be present in the composition of the present invention at concentrations of from about 0.004% w/v to about 1.5% w/v, optionally from about 0.01% w/v to about 1.2% w/v, or optionally from about 0.06% w/v to about 1.0% w/v of the total composition.

Antimicrobial Mixture

In certain embodiments, the compositions of the present invention comprise an antimicrobial mixture comprising one or more nutrient(s) and, optionally, one or more electrolyte(s).

Nutrients useful in the antimicrobial mixture of the present invention include, but are not limited to, lactate salts (such as sodium lactate or potassium lactate), phosphate salts (such as sodium phosphate, disodium phosphate and potassium phosphate), monosaccharides (such as glucose, fructose or galactose), disaccharides, citrates (such as citric acid, sodium citrate, potassium citrate) and mixtures thereof.

In certain embodiments, the nutrients include (are selected from or selected from the group consisting of) lactate, glucose and mixtures thereof. The present inventors have observed that glucose provides a significant contribution to the antifungal activity of the antimicrobial mixtures. The lactate follows the glucose with regard to the significance of its contribution to the antifungal activity of the antimicrobial mixture. And, in certain embodiments, when combined with the glucose, the lactate/glucose combination provides an even higher degree of the antifungal activity than glucose alone.

While it was observed that citrate, ascorbic acid or glycine, individually, contribute minimally to the antifungal activity of the antimicrobial mixture, it was found that the combination of citrate, lactate and glycine was observed to improve the antifungal contribution of each of the glucose or lactate to the antimicrobial mixture, with the largest improvement observed when the glucose and lactate are combined with citrate, ascorbic acid and glycine.

In certain embodiments, the antimicrobial mixture further comprises electrolytes useful in the antimicrobial mixture of the present invention include, but are not limited to, alkaline earth metal salts, such as alkaline earth metal inorganic salts, and mixtures thereof. Suitable examples include potassium salts such as potassium chloride and potassium phosphate), magnesium salts (such as magnesium chloride), sodium salts (such as sodium chloride); counter anions such as chloride and mixtures thereof.

In certain embodiments, the nutrient(s) and electrolyte(s) are present in the antimicrobial mixture such that when incorporated to form the compositions of the present invention: i) the total nutrient concentration, in the total composition of the present invention, is from about 1.0 mMol/L to about 4.0 mMol/L, optionally from about 2.0 mMol/L to about 3.0 mMol/L, or optionally from about 2.8 mMol/L to about 3.0 mMol/L of the composition; and, when incorporated, ii) the total electrolyte concentration, in the total composition of the present invention, is from about 20 mMol/L to about 80.0 mMol/L, optionally from about 30 mMol/L to about 70 mMol/L, or optionally from about 40 mMol/L to about 60 mMol/L of the composition In certain embodiments, one or more, optionally two or more, optionally three of more, optionally four or more of the nutrients and, optionally, one or more, optionally two or more, optionally three of more, optionally four or more of the electrolytes are present in the antimicrobial mixture such that:

A. the total nutrient concentration in the composition of the present invention comprises the individual nutrients in the following concentrations:
  i) a lactate concentration of from about 0 mMol/L to about 10.0 mMol/L, optionally from about 1.0 mMol/L to about 6.0 mMol/L; or optionally 2.0 mMol/L to about 3.0 mMol/L of the total composition;
  ii) a citrate concentration of from about 0 mMol/L to about 0.5 mMol/L, optionally from about 0.01 mMol/L to about 0.10 mMol/L; or optionally 0.025 mMol/L to about 0.050 mMol/L of the total composition;
  iii) a phosphate concentration of from about 0 mMol/L to about 10 mMol/L, optionally from about 1 mMol/L to about 5 mMol/L; or optionally 1.5 mMol/L to about 2.5 mMol/L of the total composition;
  iv) a glucose concentration of from about 0.1 mMol/L to about 25 mMol/L, optionally from about 0.1 mMol/L to about 10 mMol/L; or optionally 0.1 mMol/L to about 0.4 mMol/L of the total composition;
and
B. optionally, the total electrolyte concentration in the total composition of the present invention comprises the individual electrolytes in the following concentrations:
  i) a potassium concentration of from about 24 mMol/L to about 28 mMol/L of the total composition;
  ii) a sodium concentration of from about 5 mMol/L to about 10 mMol/L of the total composition;
  iii) a magnesium concentration of from about 0.50 mMol/L to about 0.80 mMol/L of the total composition;
  iv) a chloride concentration of from about 23 mMol/L to about 28 mMol/L of the total composition.

In certain embodiments, ascorbic acid is present at a concentration not exceeding 0.001% w/v, optionally at from about 0.00002% w/v to about 0.0001% w/v, or optionally from about 0.00001% w/v to about 0.00002% w/v, of the total composition.

In certain embodiments, the antimicrobial mixture is free of, or substantially free of, calcium, bicarbonate, low molecular weight amino acids and/or zinc ions. The term "substantially free" as used herein means a concentration less than 1% (or about 1%), optionally, less than 0.1% (or about 0.1%), optionally less than 0.01% (or about 0.01%), optionally less than 0.001% (or about 0.0.001%), or optionally less than 0.0001% (or about 0.0001%). Examples of low molecular weight amino acids include, but are not limited to, L-alanine, β-alanine, α-aminoadipic acid, α-aminobutyric acid, γ-aminobutyric acid, α-aminoisobutyric acid, arginine, asparagine, aspartic acid, citrulline, creatine, glutamic acid, glycine, histidine, cysteine, leucine, lysine, norleucine, ornithine, phenylalanine, phophoserine, sarcosine, threonine and valine.

In certain embodiments, glycine is present at a concentration not exceeding 0.0010% w/v, optionally at from about 0.00001% w/v to about 0.0002% w/v, or optionally from about 0.00002% w/v to about 0.0001% w/v, of the total composition.

The inventors further observed that mono- and di-saccharides such as glucose actually improve the antifungal activity of polyquaternium compounds such as polyquaternium 42. This is surprising as glucose agar medium is prescribed to preculture fungi for availability in preservative efficacy testing.

Monosaccharides suitable for use with the polyquaternium compounds either alone, or as part of the antimicrobial mixture include, but are not limited to (or, are selected from, or selected from the group consisting of), glucose, fructose, galactose, isomers thereof and mixtures thereof.

Disaccharides suitable for use with the polyquaternium compounds either alone or as part of the antimicrobial mixture include, but are not limited to (or, are selected from, or selected from the group consisting of), sucrose, lactulose, lactose, maltose, α,α-trehalose, β,β-trehalose, α,β-trehalose, cellobiose, chitobiose, kojibiose. nigerose, isomaltose, sophorose, laminaribiose, gentiobiose, turanose, maltulose, palatinose, gentiobiulose, mannobiose, melibiose, melibiulose, rutinose, rutinulose, xylobiose, isomers thereof and mixtures thereof.

In certain embodiments, the mono- and/or di-saccharides is present in compositions containing the polyquaternium compound at a concentration of from about 0.002% w/v to 1% (or about 1%) w/v, optionally at from about 0.002% w/v to about 0.8% w/v, or optionally at from about 0.003% w/v to about 0.4% w/v, of the total composition.

Polyol

In certain embodiments, the compositions of the present invention may further comprise a polyol or combination of polyols. In certain embodiments, the presence of additional components such as the pharmaceutically active compounds may require the addition of a polyol or combination of polyols. As used herein, and unless otherwise indicated, the term "polyol" shall refer to any compound having at least two —OH groups. The polyols can be linear or circular, substituted or unsubstituted, or mixtures thereof, so long as the resultant complex is water-soluble and pharmaceutically acceptable. Such polyol compounds include sugars, sugar alcohols, sugar acids, uronic acids and mixtures thereof. In certain embodiments, the polyols are sugars, sugar alcohols and sugar acids, including, but not limited to: mannitol, glycerin (glycerol), propylene glycol, polyethylene glycol, sorbitol and mixtures thereof. In certain embodiments, the polyols are polysorbate 80, mannitol, sorbitol, propylene glycol, polyethylene glycol, glycerin or mixtures thereof. In certain embodiments, the polyol is glycerin. In other embodiments, the polyol is a combination of polyols such as glycerin and propylene glycol or glycerin and sorbitol.

The polyol (or combinations thereof) can optionally, be present in the composition of the present invention at concentrations of from about 0.2% w/v to about 2.0% w/v, optionally from about 0.2% w/v to about 1.7% w/v, or optionally from about 0.4% w/v to about 1.5% w/v of the total composition.

Optional Components

The compositions of the present invention may further optionally comprise one or more additional excipients and/or one or more additional active ingredients. Excipients commonly used include, but are not limited to, demulcents, tonicity agents, preservatives, chelating agents, buffering agents (other than and in addition to the organic acids of the present invention), and surfactants. Other excipients comprise solubilizing agents, stabilizing agents, comfort-enhancing agents, polymers, emollients, pH-adjusting agents (other than and in addition to the organic acids of the present invention), and/or lubricants. Any of a variety of excipients may be used in the compositions of the present invention including water, mixtures of water and water-miscible solvents, such as vegetable oils or mineral oils comprising from 0.5% to 5% non-toxic water-soluble polymers, natural products, such as agar and acacia, starch derivatives, such as starch acetate and hydroxypropyl starch, and also other synthetic products such as polyvinyl alcohol, polyvinylpyrrolidone, polyvinyl methyl ether, polyethylene oxide, and preferably cross-linked polyacrylic acid and mixtures thereof.

Demulcents or soothing agents used with embodiments of the present invention, in addition to the cellulose derivatives include, but are not limited to, glycerin, polyvinyl pyrrolidone, polyethylene oxide, polyethylene glycol, propylene glycol and polyacrylic acid. In certain embodiments, propylene glycol and polyethylene glycol 400 are the demulcents. In certain embodiments, glycerin, in addition to its use as a tonicity adjusting agent, can also act as a demulcent.

Tonicity-adjusting agents may also be, optionally, used in the compositions of the present invention. Suitable tonicity-adjusting agents include, but are not limited to, mannitol, sodium chloride, glycerin, and the like. Suitable buffering agents include, but are not limited to, phosphates, borates, acetates and the like, and amino alcohols such as 2-amino-2-methyl-1-propanol (AMP), salts of any of the above and mixtures of any of the above mentioned agents.

Suitable surfactants include, but are not limited to, ionic and nonionic surfactants (though nonionic surfactants are preferred), RLM 100, POE 20 cetylstearyl ethers such as Procol® CS20, poloxamers such as Pluronic® F68, and block copolymers such as poly(oxyethylene)-poly(oxybutylene) compounds set forth in U.S. Patent Application Publication No. 2008/0138310 entitled "Use of PEO-PBO Block Copolymers in Ophthalmic Compositions" filed Dec. 10, 2007 (which publication is herein incorporated by reference).

Also useful herein are polyethoxylated castor oil compounds classified as PEG-2 to PEG-200 castor oils, as well as those classified as PEG-5 to PEG-200 hydrogenated castor oils. Such polyethoxylated castor oils include those manufactured by Rhone-Poulenc (Cranbury, N.J.) under the Alkamuls® brand, those manufactured by BASF (Parsippany, N.J.) under the Cremophor® brand, and those manufactured by Nikko Chemical Co., Ltd. (Tokyo, Japan) under the Nikkol brand. In certain embodiments, the polyethoxylated castor oils are those classified as PEG-15 to PEG-50 castor oils or, optionally, PEG-30 to PEG-35 castor oils. In some embodiments, polyethoxylated castor oils known as Cremophor® EL and Alkamuls® EL-620 are used. In other embodiments, polyethoxylated hydrogenated castor oils classified as PEG-25 to PEG-55 hydrogenated castor oils are used. In one embodiment, the polyethoxylated hydrogenated castor oil is PEG-40 hydrogenated castor oil, supplied as Lumulse GRH-40 by VANTAGE (GURNEE, Ill., USA).

In general, the present invention can include one or more polyethoxylated castor oils in an amount from about 0.02% to about 20% by weight (wt %) of the total composition. In certain embodiments, one or more polyethoxylated castor oils may be used in an amount of from about 0.05 wt % to about 5 wt %, or, optionally, from about 0.1 wt % to about 2 wt % of the total composition. Mixtures of any of the above polyethoxylated castor oils and polyethoxylated hydrogenated castor oils can also be used.

Compositions of the present invention are ophthalmologically suitable for application to a subject's eyes. The term "aqueous" used in describing an aqueous formulation, or an aqueous component of the total composition, wherein the excipient is greater than about 50%, optionally greater than about 75%, or optionally greater than about 90% by weight water. These drops may be delivered from a single dose ampoule which may preferably be sterile and thus render microcidal or bacteriostatic/fungistatic components of the formulation unnecessary. Alternatively, the drops may be delivered from a multi-dose bottle which may preferably comprise a device which extracts any preservative from the composition as it is delivered, such devices being known in the art.

In certain embodiments, the compositions of the present invention are isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The compositions of the present invention generally have an osmolality in the range of 220-320 mOsm/kg, or, optionally, have an osmolality in the range of 235-300 mOsm/kg. The ophthalmic compositions will generally be formulated as sterile aqueous solutions.

In a useful embodiment, the compositions of the present invention include hydrophobic components. Any suitable hydrophobic component may be employed in the present invention. In one embodiment, the hydrophobic component may be considered as comprising a discontinuous phase in the compositions of the present invention, for example, oil-in-water emulsions.

The hydrophobic component may be present in an effective amount, for example, in an amount of up to about 1.0% by weight or about 1.5% by weight of the total composition.

In certain embodiments, the hydrophobic component comprises one or more oily materials. Examples of useful oil materials include, without limitation, vegetable oils, animal oils, mineral oils, synthetic oils and the like and mixtures thereof. In one embodiment, the hydrophobic component comprises one or more higher fatty acid glycerides. In another embodiment, the hydrophobic component comprises castor oil. Other embodiments, the oil component is combined with the above mentioned surfactants (e.g., in certain embodiments, the polyethoxylated castor oil and/or polyethoxylated hydrogenated castor oil surfactants) in the aqueous formulations to form emulsions.

In one embodiment, the presently useful compositions are self-emulsifying which, when exposed to an aqueous medium, form fine oil-in-water emulsions with little or no agitation. Additionally, emulsions may be prepared by combining a self-emulsifying pre-concentrate with an aqueous medium. Previously-disclosed self-emulsifying systems include those comprising mixtures of (i) medium-chain triglycerides and nonionic surfactants, (ii) vegetable oils and partial glycerides, such as polyglycolized glycerides or medium-chain mono- and diglycerides, or (iii) vegetable oils and nonionic surfactants such as polysorbate 80, PEG-25 glyceryl trioleate, polyethoxylated castor oils and/or polyethoxylated hydrogenated castor oils.

The compositions of the present invention can also be used to administer pharmaceutically active compounds. Such compounds include, but are not limited to, (or selected from or selected from the group consisting of) glaucoma therapeutics, pain relievers, anti-inflammatory, vaso-constrictors, dry eye relievers and anti-allergy medications, and anti-infectives. More specific examples of pharmaceutically active compounds include betaxolol, timolol, pilocarpine or pharmaceutically acceptable salts thereof; carbonic anhydrase inhibitors or pharmaceutically acceptable salts thereof prostglandins; dopaminergic antagonists; post-surgical antihypertensive agents, such as para-amino clonidine (apraclonidine) or pharmaceutically acceptable salts thereof; anti-infectives such as ciprofloxacin, moxifloxacin, tobramycin or pharmaceutically acceptable salts thereof; non-steroidal and steroidal anti-inflammatories, such as naproxen, diclofenac, nepafenac, suprofen, ketorolac, tetrahydrocortisol, dexamethasone or pharmaceutically acceptable salts thereof; dry eye therapeutics or pharmaceutically acceptable salts thereof such as PDE4 inhibitors; vaso-contrictors such as tetrahydrozoline, naphazoline, oxymetazoline, ephedrine, phenylephrine or pharmaceutically acceptable salts thereof; anti-allergy medications or pharmaceutically acceptable salts thereof such as H1/H4 inhibitors, H4 inhibitors, olopatadine; and dry eye relievers such as tamarind seed extract, hyaluronic acid and guar gum (including high performance guar gum); or mixtures of any of the above mentioned actives or categories of actives.

In certain embodiments, the compositions of the present invention further include one of more retinoids. Retinoids include Vitamin A (retinol), retinoic acid, and retinyl palmitate as well as related compounds that are synthetic or naturally occurring cellular components or metabolites. The effects of RA and synthetic derivatives are mediated by two classes of nuclear receptors, the retinoic acid receptors which belong to the erbA-related steroid/thyroid nuclear receptor superfamily and the retinoid X receptors which also belong to the same super family of steroid/thyroid hormones (Gorodeski, et al., Am. J. Physiol. Cell. Physiol. 275, 758-765 (1998).

Vitamin A and related retinoids are involved in the maintenance of mucosal membranes via control of the proliferation and differentiation of epithelial cells. A deficiency of retinoids results in a gradual change of the ocular mucosa to a non-secretory keratinized epithelium. (Kobayashi, et al., Ophthalmologica, 211, 358-361 (1997)). Retinoic acid plays a fundamental role in cell proliferation, and cell differentiation and it may also prevent malignant transformation (Darmon, 1991, Sem. Dev. Biol. 2:219).

Retinoids have been utilized to treat a number of conditions involving keratinization of epithelial tissue, including: acne vulgaris, psoriasis, wound healing and premalignant lesions (Kligman, A., Cutis, 39, 486-488 (1987). Formulations containing retinoids have also been utilized to treat ocular disorders involving the epithelium, such as dry eye, Stevens-Johnson syndrome (Kobayashi, et al., Ophthalmologica, 211, 358-361 (1997); Selek, et al., Eur. J. Ophthalmol, 10, 121-127 (2000) and Kim, et al., Amer. J. Oph, 147, 206-213.e3 (2009)). Topical retinoid formulations include ointments and liquid formulations that may be applied 2-4 times per day for one or more months. Increases in goblet cell density in ocular mucosal tissue, tear break up time and Schirmer score measurements have been noted following topical retinoid therapy.

In certain embodiments, the compositions of the present invention further comprise one or more fatty acid esters such as 1-3 carbon monohydric or 4-10 carbon polyol esters of: alpha-linolenate, dihomogamma-linolenic acid, gamma-linolenate, eicosapentaenoic acid or docosahexaenoic acid (e.g., ethyl alpha-linolenate or ethyl gamma-linolenate). Mixtures of any such fatty acid esters may also be used herein. Suitable monohydric and/or polyol fatty acid esters are detailed in US patent publications US20130005805A1 and US20140364400A1, each of which are herein incorporated by in its entirety.

It is also contemplated that the concentrations of the ingredients comprising the formulations of the present invention can vary. A person of ordinary skill in the art would understand that the concentrations can vary depending on the addition, substitution, and/or subtraction of ingredients in a given formulation.

In certain embodiments, the compositions of the present invention are buffered, using buffering agents, such that the compositions maintain a pH of from about 5.0 to a pH of about 8.0, optionally a pH of from about 6.5 to a pH of about 8.0. Topical formulations (particularly topical ophthalmic formulations, as noted above) are preferred which have a physiological pH matching the tissue to which the formulation will be applied or dispensed.

In certain embodiments, the compositions of the present invention is in the form of eye-drop solution, eye wash solution, contact lens packing solutions, contact lens lubricating, rewetting and/or rinsing solution, spray, mist or any other manner of administering a composition to the eye.

In particular embodiments, the composition of the present invention are formulated for administration at any frequency of administration, including once a week, once every five days, once every three days, once every two days, twice a day, three times a day, four times a day, five times a day, six times a day, eight times a day, every hour, or greater frequency. Such dosing frequency is also maintained for a varying duration of time depending on the therapeutic needs of the user. The duration of a particular therapeutic regimen may vary from one-time dosing to a regimen that extends for months or years. One of ordinary skill in the art would be familiar with determining a therapeutic regimen for a specific indication.

EXAMPLES

The compositions of the present invention as described in following examples illustrate specific embodiments of compositions of the present invention, but are not intended to be limiting thereof. Other modifications can be undertaken by the skilled artisan without departing from the spirit and scope of this invention.

TABLE 1

Comparative and Inventive examples of the Compositions of the Present Invention

| INGREDIENT | 1A (Comparative Example) Dry Eye Compositions | | 1B (Comparative Example) Dry Eye Compositions | | 1C (Inventive Example) Useful for Relief of Dry Eye Irritation (with or without Contact Lenses) | | 1D (Inventive Example) Useful for Relief of Dry Eye Irritation (with or without Contact Lenses) | | 1E (Inventive Example) Useful for Relief of Dry Eye Irritation (with or without Contact Lenses) | |
|---|---|---|---|---|---|---|---|---|---|---|
| | % w/w | amount per batch (gms) | % w/w | amount per batch (gms) | % w/w | amount per batch (gms) | % w/w | amount per batch (gms) | % w/w | amount per batch (gms) |
| Sodium Hyaluronate[1] | 0.25 | 1.25 | 0.1 | 0.2 | 0.10 | 1.00 | 0.120 | 1.20 | 0.120 | 0.60 |
| Tamarind Seed Polysaccharide[2] | 0.25 | 1.25 | | | 0.10 | 1.00 | 0.200 | 2.00 | 0.200 | 1.00 |
| Polyethylene Glycol 400[3] | | | | | | | 1.118 | 11.18 | 1.118 | 5.59 |
| Glycerin | | | | | | | 0.2502 | 2.502 | 0.2502 | 1.251 |
| Hypromellose E3 2910[4] | | | 0.3 | 0.6 | 0.30 | 3.0 | 0.198 | 1.98 | 0.198 | 0.99 |
| Boric Acid[5] | | | | | | | 0.80 | 8.0 | 0.80 | 4.0 |
| Sodium Borate[6] | | | | | | | 0.045 | 0.45 | | |
| Disodium Phosphate[7] | | | | | | | 0.027 | 0.27 | 0.027 | 0.135 |
| Sodium Citrate Dihydrate[8] | | | | | | | 0.20 | 2.0 | 0.20 | 1.0 |
| Sodium Chloride[9] | 0.87 | 4.35 | 0.87 | 1.74 | 0.88 | 8.8 | | | | |
| Potassium Chloride[10] | | | | | | | 0.10 | 1.0 | 0.179 | 0.895 |
| 50% Aqueous Solution of Sodium Lactate[11] | | | | | | | 0.057 | 0.57 | 0.057 | 0.285 |
| Magnesium Chloride[12] | | | | | | | 0.013 | 0.13 | 0.013 | 0.065 |
| Glucose[13] | | | | | | | 0.0036 | 0.036 | 0.0036 | 0.018 |
| Glycine[14] | | | | | | | 0.00002 | 0.0002 | 0.00002 | 0.0001 |
| Ascorbic Acid[15] | | | | | | | 0.00001 | 0.0001 | 0.00001 | 0.00005 |
| IN Sodium Hydroxide[16] | 0.003 | 0.015 | 0.003 | 0.006 | 0.001 | 0.01 | | | | |
| Disodium Edetate [17] | | | | | | | 0.01 | 0.1 | 0.05 | 0.25 |
| Polyquaternium 42[18] | | | | | | | | | 0.0030 | 0.015 |
| Purified Water | 98.627 | 493.135 | 98.727 | 197.454 | 98.619 | 986.20 | 96.8517 | 968.52 | 96.78117 | 483.91 |
| total | 100.00% | 500.00 g | 100.00% | 200.00 g | 100.00% | 1000.00 g | 100.00% | 1000.00 g | 100.00% | 500.00 g |

[1]Research Grade, HA15M Supplied by LIFECORE (CHASKA, MINNESOTA, US).
[2]Supplied by FARMIGEA (OSPEDALETTO, ITALY)
[3]Supplied by Clariant Produkte (BURGKIRCHEN, GERMANY)
[4]Hydroxypropylmethyl cellulose supplied by DOW CHEMICAL (PLAQUEMINE, LOUISIANA, USA)
[5]Supplied by Merck KGaA (DARMSTADT, GERMANY)
[6]Supplied by Merck KGaA (DARMSTADT, GERMANY)
[7]Supplied by Merck KGaA (DARMSTADT, GERMANY)
[8]Supplied by Merck KGaA (DARMSTADT, GERMANY)
[9] Supplied by Caldic (DUSSELDORF, GERMANY)
[10]Potassium Chloride was supplied by KGaA (DARMSTADT, GERMANY)
[11]Supplied as Sodium Lactate (50% aqueous) by Merck KGaA (DARMSTADT, GERMANY)
[12]Supplied by KGaA (DARMSTADT, GERMANY)
[13]Supplied by Roquette Freres (LASTREM, FRANCE)
[14]Supplied by Merck KGaA (DARMSTADT, GERMANY)
[15]Supplied by DSM NUTRITIONAL Products (DRAKEMYRE, SCOTLAND, UK)
[16]Supplied by VWR (RADNER, PA)
[17] Supplied by Merck NV/SA (OVERIJSE, BELGIUM)
[18]Supplied as Polyquatemium 42 (33% aqueous) by DSM BIOMEDICAL, (BERKELEY, CA)

The procedure for preparing solution 1A was as follows:
1. To an 800 ml beaker is added 450 grams of Purified Water USP.
2. To the composition of step 1 is added 1.25 g of Sodium Hyaluronate. The solution is mixed until the Sodium Hyaluronate dissolved.
3. To the solution of step 2 is added 1.25 g of Tamarind Seed Polysaccharide. The solution is mixed until the Tamarind Seed Polysaccharide dissolved.
4. Next is added 4.35 g of Sodium Chloride to the solution of step 3. The solution is mixed until all the Sodium Chloride is dissolved.
5. To the solution of Step 4, 0.15 gram of a premixed solution of 1 gram of 1 N Sodium Hydroxide solution in 9 grams of Purified Water is added.
6. Additional water is added to the solution of step 5 to bring the weight of the solution to a total of 500.00 grams and the solution is mixed for an additional 10 minutes.

Results: The solution has a surface tension of 68.06, as measured by the Rame-Hart—DROPimage Advanced Software Pendant Drop Method described above, which is greater than about 40.8 dynes/cm to 51.9 dynes/cm of the present invention and is not expected to have rapid and extensive rewetting of eyes because of such high surface tension.

The procedure for preparing solution 1B was as follows:
1. To a 500 ml beaker is added 160 grams of Purified Water USP.
2. To the composition of step 1 is added 0.2 g of Sodium Hyaluronate. The solution is mixed until the Sodium Hyaluronate dissolved.
3. To the solution of step 2 is added 0.6 g of Hypromellose E3 Premium. The solution is mixed until the Hypromellose E3 Premium dissolved.

4. Next is added 1.74 g of Sodium Chloride to the solution of step 3. The solution is mixed until all the Sodium Chloride is dissolved.
5. To the solution of Step 4, 0.06 gram of a premixed solution of 1 gram of 1 N Sodium Hydroxide solution in 9 grams of purified water is added.
6. Additional water is added to the solution of step 6 to bring the weight of the solution to a total of 200.00 grams and the solution is mixed for an additional 10 minutes.

Results: The solution has a viscosity of 24 cps as measured by the AR2000 Flow Test Method described above, which falls outside of the about 50 cps to about 100 cps viscosity range of the present invention and is not expected to have sufficient substantivity and/or moisturization to permit retention on the ocular surface for improved tear stability for dry eye relief.

The procedure for preparing solution 1C was as follows:
1. To a 1500 ml beaker is added 900 grams of Purified Water USP.
2. To the composition of step 1 is added 0.1 g of Sodium Hyaluronate. The solution is mixed until the Sodium Hyaluronate dissolved.
3. To the solution of step 2 is added 0.1 g of Tamarind Seed Polysaccharide. The solution was mixed until the Tamarind Seed Polysaccharide dissolved.
4. To the solution of step 3 is added 0.3 g of Hypromellose E3 Premium. The solution was mixed until the Hypromellose E3 Premium dissolved.
5. Next is added 8.8 g of Sodium Chloride to the solution of step 4. The solution is mixed until all the Sodium Chloride is dissolved.
6. To the solution of Step 5, 0.10 gram of a premixed solution of 1 gram of 1 N Sodium Hydroxide dissolved in 9 grams of Purified Water.
7. Additional water is added to the solution of step 6 to bring the weight of the solution to a total of 1000.00 grams and the solution is mixed for an additional 10 minutes.

Results: The solution has a viscosity 86.0 cps., as measured by the AR2000 Flow Test Method described above, which falls within the about 50 cps to about 100 cps viscosity range of the present invention and is expected to have sufficient substantivity and/or moisturization to permit retention on the ocular surface for improved tear stability for dry eye relief The procedure for preparing solution 1D was as follows:
1. To a 1500 ml beaker is added 800 grams of Purified Water USP.
2. To the beaker of step 1 is added 1.2 g of Sodium Hyaluronate. The solution is mixed until the Sodium Hyaluronate is dissolved.
3. To the solution of step 2 is added 0.2 g of Tamarind Seed Polysaccharide. The solution is mixed until the Tamarind Seed Polysaccharide is dissolved.
4. To the solution of step 3 is added 1.98 g of Hypromellose E3 Premium. The solution is mixed until the Hypromellose E3 Premium is dissolved.
5. Into a separate 150 ml beaker is added 95 g of Purified Water.
6. To the beaker in step 5 is added 0.02 grams of Glycine and 0.01 grams of Ascorbic acid. The solution is mixed until the Glycine and Ascorbic acid are dissolved.
7. An additional 4.97 grams of water is added to the solution of step 6 and mixed until the solution was uniform.
8. To the solution of Step 4 is added 2.0 grams of Sodium Citrate. The Sodium Citrate is mixed into the solution for at least 10 minutes until dissolved.
9. To the solution of Step 8 are added the following ingredients while mixing, allowing time for each to dissolve completely before adding the next: 0.27 grams of Disodium Phosphate, 0.13 grams of Magnesium Chloride, 1.0 grams of Potassium Chloride, 0.036 grams of Glucose, and 0.45 grams of Sodium Borate, allowing each ingredient to mix before adding the next.
10. To the solution of Step 9, 2.5 grams of Glycerin and 11.18 grams of Polyethylene Glycol 400 are slowly added while mixing, allowing for each ingredient to completely dissolve before the next ingredient is added.
11. To the solution of Step 10, 8.0 grams of Boric acid and 0.57 g of Sodium Lactate are slowly added while mixing and mixed until completely dissolved.
12. To the solution of Step 11 is added 1.0 gram of the solution prepared in step 7.
13. To the solution of step 12 is added 0.1 grams of Disodium Edetate.
14. The solution of step 13 is mixed until completely dispersed.
15. Sufficient water is added to solution of step 14 to bring the weight of the solution of Step 13 to 1000.00 grams and the solution was mixed for an additional 10 minutes.

Results: The solution has a viscosity of 72.2 cps, as measured by the AR2000 Flow Test Method described above, which falls within the about 50 cps to about 100 cps viscosity range of the present invention and is expected to have sufficient substantivity and/or moisturization to permit retention on the ocular surface for improved tear stability for dry eye relief The procedure for preparing solution 1E was as follows:
1. To a 1000 ml beaker was added 400 grams of Purified Water USP.
2. To the beaker of step 1 was added 0.6 g of Sodium Hyaluronate. The solution was mixed until the Sodium Hyaluronate dissolved.
3. To the solution of step 2 is added 0.1 g of Tamarind Seed Polysaccharide. The solution is mixed until the Tamarind Seed Polysaccharide is dissolved.
4. To the solution of step 3 is added 0.99 g of Hypromellose E3 Premium. The solution is mixed until the Hypromellose E3 Premium is dissolved.
5. Into a separate 150 ml beaker is added 95 g of Purified Water.
6. To the beaker in step 5 is added 0.01 grams of Glycine and 0.005 grams of Ascorbic acid. The solution is mixed until the Glycine and Ascorbic acid are dissolved.
7. An additional 4.97 grams of water is added to the solution of step 6 and mixed until the solution was uniform.
8. To the solution of Step 4 is added 1.0 grams of Sodium Citrate. The Sodium Citrate is mixed into the solution for at least 10 minutes until dissolved.
9. To the solution of Step 8 are added the following ingredients while mixing, allowing time for each to dissolve completely before adding the next: 0.135 grams of Disodium Phosphate, 0.065 grams of Magnesium Chloride, 0.895 grams of Potassium Chloride, and 0.018 grams of Glucose, allowing each ingredient to mix before adding the next.
10. To the solution of Step 9, 1.25 grams of Glycerin and 5.59 grams of Polyethylene Glycol 400 are slowly added while mixing, allowing for each ingredient to completely dissolve before the next ingredient is added.
11. To the solution of Step 10, 4.0 grams of Boric acid and 0.285 g of Sodium Lactate aree slowly added while mixing and mixed until completely dissolved.

12. To the solution of Step 11 is added 1.0 gram of the solution prepared in step 7.
13. To the solution of step 12 is added 0.25 grams of Disodium Edetate.
14. The solution of step 13 is mixed until completely dispersed.
15. To the solution in step 14 is added 0.045 grams of a 33% solution of Polyquaternium 42 in water.
16. Sufficient water is added to solution of step 15 to bring the weight of the solution of Step 15 to 500.00 grams and the solution is mixed for an additional 10 minutes.

Results: The solution has a viscosity of 68.6 cps as measured by the AR2000 Flow Test Method described above, within the about 50 cps to about 100 cps viscosity range of the present invention and is expected to have sufficient substantivity and/or moisturization to permit retention on the ocular surface for improved tear stability for dry eye relief.

For Examples 2A: The Potassium Chloride can be supplied by KGaA (DARMSTADT, GERMANY).

For Example 2A: The Sodium Chlorite Dihydrate can be supplied by Oxychem (WICHITA, Kans., USA)

For Example 2B: The Polyquaternium-42 (33% aqueous) can be supplied by DSM BIOMEDICAL (BERKELEY, Calif., USA)

For Examples 2A-2C: The Lumulse GRH-40 can be supplied by VANTAGE (GURNEE, Ill., USA).

For Examples 2A-2C: The Super refined Castor Oil can be supplied by CRODA (EDISON, N.J., USA).

For Examples 2B-2C: The Ethyl linolenate can be supplied by SIGMA-ALDRICH (ST. LOUIS, Mo., USA).

For Examples 2B-2C: The Retinyl Palmitate can be supplied by SIGMA-ALDRICH (ST. LOUIS, Mo., USA).

For Examples 2B-2C: The Sodium Citrate Dihydrate can be supplied by Merck KGaA (DARMSTADT, GERMANY).

TABLE 2

Prophetic Examples of the Compositions of the Present Invention

| INGREDIENT | 2A Useful for Relief of Dry Eye Irritation % w/w | 2A amount per batch (gms) | 2B Useful for Relief of Dry Eye Irritation % w/w | 2B amount per batch (gms) | 2C Useful for Relief of Dry Eye Irritation % w/w | 2C amount per batch (gms) |
|---|---|---|---|---|---|---|
| Sodium Hyaluronate | 0.10 | 1.0 | 0.10 | 1.0 | 0.10 | 1.0 |
| Tamarind Seed Polysaccharide | 0.10 | 1.0 | 0.20 | 2.0 | 0.10 | 1.0 |
| Hypromellose 2910 | 0.30 | 3.0 | 0.30 | 3.0 | 0.30 | 3.0 |
| Polyethylene Glycol 400 | 0.25 | 2.5 | 0.25 | 2.5 | 0.25 | 2.5 |
| Boric Acid | 0.60 | 6.0 | 0.60 | 6.0 | 0.60 | 6.0 |
| Sodium Borate | 0.035 | 0.35 | 0.05 | 0.50 | 0.05 | 0.50 |
| Sodium Chloride | 0.05 | 0.50 | 0.05 | 0.50 | 0.05 | 0.50 |
| Calcium Chloride | 0.006 | 0.060 | 0 | 0 | 0 | 0 |
| Magnesium Chloride | 0.006 | 0.060 | 0 | 0 | 0 | 0 |
| Potassium Chloride | 0.14 | 1.40 | 0 | 0 | 0 | 0 |
| Sodium Citrate Dihydrate | 0 | 0 | 0.65 | 6.50 | 0.65 | 6.50 |
| Super refined Castor Oil | 0.625 | 6.25 | 0.625 | 6.25 | 0.625 | 6.25 |
| Lumulse GRH-40 | 0.50 | 5.0 | 0.50 | 5.0 | 0.50 | 5.0 |
| Ethyl linolenate | 0 | 0 | 0.0502 | 0.502 | 0.0502 | 0.502 |
| Retinyl Palmitate | 0 | 0 | 0.0502 | 0.502 | 0.0502 | 0.502 |
| Sodium Chlorite | 0.014 | 0.140 | 0 | 0 | 0 | 0 |
| Polyquatemium 42 (33% aqueous) | 0 | 0 | 0.0090 | 0.090 | 0 | 0 |
| Purified Water* | | | | | | |
| total | 100.00% | 1000.0 g | 100.00% | 1000.0 g | 100.00% | 1000.0 g |

*q.s to 100% w/w

For Examples 2A-2C: The Sodium Hyaluronate can be supplied by CONTIPRO A.S. (DOLNI, DOBROUC, CZECH REPUBLIC).

For Examples 2A-2C: The Tamarind Seed Extract can be supplied by INDENA (MILAN, ITALY).

For Examples 2A-2C: The Hypromellose 2910 is HPMC E3 Premium can be supplied by DOW CHEMICAL (PLAQUAMINE, LOUISIANA, USA).

For Examples 2A-2C: The Polyethylene Glycol 400 can be supplied by Clariant Produkte (BURGKIRCHEN, GERMANY).

For Examples 2A-2C: The Boric Acid can be supplied by Merck KGaA (DARMSTADT, GERMANY).

For Examples 2A-2C: The Sodium Borate can be supplied by Merck KGaA (DARMSTADT, GERMANY).

For Examples 2A-2C: The Sodium Chloride can be supplied by Caldic (DUSSELDORF, GERMANY).

For Examples 2A: The Calcium Chloride Dihydrate can be supplied by Merck KGaA (DARMSTADT, GERMANY).

For Examples 2A: The Magnesium Chloride can be supplied by KGaA (DARMSTADT, GERMANY).

The procedure for preparing solution 2A can be as follows:
1. To a 50 ml beaker is added 5.0 grams of Lumuluse GRH-40
2. While mixing, 6.25 grams of Super refined Castor Oil is added.
3. The above is mixed until homogeneous.
4. In a separate 1500 ml beaker is added 900 grams of Purified Water.
5. To the above is added 1.0 gram of Sodium Hyaluronate. The solution is mixed to fully dissolve the Sodium Hyaluronate.
6. To the above is added 1.0 gram of Tamarind Seed Polysaccharide.
   The solution is mixed until the Tamarind Seed Polysaccharide is fully dissolved.
7. To the above solution is next added 3.0 grams of Hypromellose 2910 E3 Premium.
8. The solution is mixed until fully dissolved.
9. The following ingredients are next added sequentially, allowing for each to dissolve before adding the next: 2.5 grams Polyethylene Glycol 400, 6.0 grams Boric acid, 0.035 gram Sodium Borate, 0.5 gram Sodium Chloride, 0.06 gram Calcium Chloride, 0.06 gram Magnesium Chloride, and 1.40 grams of Potassium Chloride.
10. The contents of step 3 are added and mixed until uniform using a homogenizer.
11. Next is added 0.14 gram of Sodium Chlorite.
12. The solution is brought to 1000.0 grams using Purified Water USP and mixed for 10 minutes to be fully uniform.
13. The solution is filtered using a 0.22 micron hydrophilic filter.

The procedure for preparing solution 2B is as follows:
1. To a 50 ml beaker is added 5.0 grams of Lumuluse GRH-40
2. While mixing, 6.25 grams of Super refined Castor Oil is added.
3. To the above is added 0.502 grams of Ethyl Linolenate and 0.502 gram of Retinyl Palmitate.
4. The uniform solution is set aside for future use.
5. In a separate 1500 ml beaker is added 900 grams of Purified Water.
6. To the above is added 1.0 grams of Sodium Hyaluronate. The solution is mixed to fully dissolve the Sodium Hyaluronate.
7. Next, 2.0 grams of Tamarind Seed Polysaccharide is added. The solution is mixed to fully dissolve the Tamarind Seed Polysaccharide.
8. To the above is added 3.0 grams of Hypromellose 2910 E3 Premium.
9. The solution is mixed to fully dissolve the HPMC.
10. The following ingredients are next added sequentially, allowing for each to dissolve before adding the next: 2.5 grams Polyethylene Glycol 400, 6.0 grams Boric acid, 0.5 gram Sodium Borate, 0.5 gram Sodium Chloride, 6.50 grams of Sodium Citrate Dihydrate, and 0.090 grams of Polyquaternium-42 (33% aqueous).
11. The contents of step 3 are added and mixed until uniform using a homogenizer.
12. The solution is brought to 1000.0 grams using Purified Water USP and mixed for 10 minutes to be fully uniform.
13. The solution is filtered using a 0.22 micron filter.

The procedure for preparing solution 2C is as follows:
1. To a 50 ml beaker is added 5.0 grams of Lumuluse GRH-40
2. While mixing, 6.25 grams of Super refined Castor Oil is added.
3. To the above is added 0.502 grams of Ethyl Linolenate and 0.502 gram of Retinyl Palmitate.
4. The uniform solution is set aside for future use.
5. In a separate 1500 ml beaker is added 900 grams of Purified Water.
6. To the above is added 1.0 grams of Sodium Hyaluronate. The solution is mixed to fully dissolve the Sodium Hyaluronate.
7. Next, 1.0 grams of Tamarind Seed Polysaccharide is added. The solution is mixed to fully dissolve the Tamarind Seed Polysaccharide.
8. To the above is added 3.0 grams of Hypromellose 2910 E3 Premium.
9. The solution is mixed to fully dissolve the HPMC.
10. The following ingredients are next added sequentially, allowing for each to dissolve before adding the next: 2.5 grams Polyethylene Glycol 400, 6.0 grams Boric acid, 0.5 gram Sodium Borate, 0.5 gram Sodium Chloride, and 6.50 grams of Sodium Citrate Dihydrate.
11. The contents of step 3 are added and mixed until uniform using a homogenizer.
12. The solution is brought to 1000.0 grams using Purified Water USP and mixed for 10 minutes to be fully uniform.
13. The solution is filtered using a 0.22 micron filter.

Embodiments of the Present Invention

1. A composition, comprising:
   a polymer mixture comprising
      i. a cellulose derivative;
      ii a tamarind seed extract; and
      iii hyaluronic acid;
   optionally, an oil component;
   optionally, a surfactant; and
   optionally, an aqueous component
   wherein the cellulose derivative, tamarind seed extract and hyaluronic acid are combined at a ratio of: 1 to 10 parts cellulose derivative: 1 to 4 parts tamarind seed extract: 1 to 2 parts hyaluronic acid, to form the polymer mixture.
2. The composition of embodiment 1 wherein the cellulose derivative is selected from (or, selected from the group consisting of) hydroxyalkyl cellulose polymers, alkyl hydroxyalkyl cellulose polymers; methyl cellulose; methyl cellulose derivatives; hydroxymethycellulose derivatives; and mixtures thereof
3. The composition of any one of or combination of embodiments 1 and 2, wherein the hydroxyalkyl cellulose polymers are selected from (or, selected from the group consisting of) hydroxyethyl cellulose, hydroxypropyl cellulose and mixtures thereof
4. The composition of any one of or combination of embodiments 1 to 3, wherein the alkyl hydroxyalkyl cellulose polymers is cetyl hydroxyethyl cellulose.
5. The composition of any one of or combination of embodiments 1 to 4, wherein the methyl cellulose derivative is selected from (or, selected from the group consisting of) carboxymethyl cellulose, hydroxymethyl cellulose, a hydroxymethyl cellulose derivative or mixtures thereof.
6. The composition of any one of or combination of embodiments 1 to 5, wherein the hydroxymethyl cellulose derivative is selected from (or, selected from the group consisting of) hydroxypropyl methylcellulose, hydroxybutyl methyl cellulose or mixtures thereof.
7. The composition of any one of or combination of embodiments 1 to 6, wherein the total concentration of the polymer mixture of cellulose derivative, tamarind seed extract and hyaluronic acid is greater than about 0.4% to about 0.9%, by weight, of the total composition of the present invention.
8. The composition of any one of or combination of embodiments 1 to 7, the total concentration of non-ionic and anionic polymer of the compositions is from (or greater than) 0.4% (or about 0.4%) to about 1.0% (or about 1.0%), by weight, of the total composition of the present invention.
9. The composition of any one of or combination of embodiments 1 to 8, wherein the surface tension of the composition ranges from about 40.8 dynes/cm to 51.9 dynes/cm as measured by the Rame-Hart—DROPimage Advanced Software Pendant Drop Method described in the specification.
10. The composition of any one of or combination of embodiments 1 to 9, wherein the rate of moisture loss for the composition is less than 1 mg/3 minutes at 37° C. and 70% relative humidity as measured by the DVS Intrinsic Measurement System and DVS-Intrinsic Control Software Method described in the specification.

11. The composition of any one of or combination of embodiments 1 to 10, wherein the composition has a viscosity of from about 30 to 100 cps at zero shear as measured by the AR2000 Flow Test Method described in the specification.

12. The composition of any one of or combination of embodiments 1 to 11, wherein the compositions have a viscosity of less than 30 cps at the shear rate of blinking (¹/₁₀₀ sec.) as measured by the AR2000 Flow Test Method described in the specification.

13. The composition of any one of or combination of embodiments 1 to 12, wherein the composition has an elastic modulus G' greater than 0.70 (or about 0.70) Pascals and a phase angle δ of from about 40° to about 65° as measured by the Bohlin CVOR Rheometer Visco-Elastic Property Test Method described in the specification.

14. The composition of any one of or combination of embodiments 1 to 13, wherein the composition has:
   i. a surface tension ranging from about 40.8 dynes/cm to 51.9 dynes/cm as measured by the Rame-Hart—DROPimage Advanced Software Pendant Drop Method described in the specification;
   ii. a rate of moisture loss of less than 1 mg/3 minutes at 37° C. and 70% relative humidity as measured by the DVS Intrinsic Measurement System and DVS-Intrinsic Control Software Method described in the specification;
   iii. a viscosity of from about 30 to 100 cps at zero shear and a viscosity of less than 30 cps at the shear rate of blinking (¹/₁₀₀ sec.) as measured by the AR2000 Flow Test Method described in the specification; and
   iv. an elastic modulus G' greater than 0.70 (or about 0.70) Pascals and a phase angle δ of from about 40° to about 65° as measured by the Bohlin CVOR Rheometer Visco-Elastic Property Test Method described in the specification.

What is claimed is:

1. An ophthalmic composition, comprising:
   a.) a polymer mixture comprising
      i. a cellulose derivative;
      ii a tamarind seed extract; and
      iii hyaluronic acid;
   b.) a polyquaternium compound selected from polyquaternium-1, polyquaternium-10, polyquaternium-42 or mixtures;
   c.) from 0.4% w/v to about 1.5% w/v of the total composition of a polyol and
   d.) an aqueous component comprising greater than about 50% by weight, of the total composition, of water
   wherein the total concentration of the polymer mixture of cellulose derivative, tamarind seed extract and hyaluronic acid is between greater than about 0.4% to about 0.9%, by weight, of the total composition and further wherein the cellulose derivative, tamarind seed extract and hyaluronic acid are combined at a ratio of: 1 to 10 parts cellulose derivative: 1 to 4 parts tamarind seed extract: 1 to 2 parts hyaluronic acid, to form the polymer mixture such that the composition has:
      i. a viscosity of from about 30 to 100 cps at zero shear as measured by the AR2000 Flow Test Method; and
      ii. a viscosity of less than 30 cps at a shear rate of blinking of ¹/₁₀₀ sec. as measured by the AR2000 Flow Test Method
   and wherein the composition is formulated as a sterile aqueous solution.

2. The composition of claim 1 wherein the cellulose derivative is selected from (hydroxyalkyl cellulose polymers, alkyl hydroxyalkyl cellulose polymers; methyl cellulose; methyl cellulose derivatives; hydroxymethycellulose derivatives; and mixtures thereof.

3. The composition of claim 2, wherein the hydroxyalkyl cellulose polymers are selected from hydroxyethyl cellulose, hydroxypropyl cellulose and mixtures thereof.

4. The composition of claim 2, wherein the alkyl hydroxyalkyl cellulose polymers is cetyl hydroxyethyl cellulose.

5. The composition of claim 2, wherein the methyl cellulose derivative is selected from carboxymethyl cellulose, hydroxymethyl cellulose, a hydroxymethyl cellulose derivative or mixtures thereof.

6. The composition of claim 5, wherein the hydroxymethyl cellulose derivative is selected from hydroxypropyl methylcellulose, hydroxybutyl methyl cellulose or mixtures thereof.

7. The composition of claim 1, wherein any non-ionic and anionic polymers in the composition are present at a the total concentration from about 0.4% to about 1.0%, by weight, of the total composition.

8. The composition of claim 1, wherein the surface tension of the composition ranges from about 40.8 dynes/cm to 51.9 dynes/cm as measured by the Rame-Hart—DROPimage Advanced Software Pendant Drop Method.

9. The composition of claim 1, wherein the rate of moisture loss for the composition is less than 1 mg/3 minutes at 37° C. and 70% relative humidity as measured by the DVS Intrinsic Measurement System and DVS-Intrinsic Control Software Method.

10. The composition of claim 1, wherein the composition has an elastic modulus G' greater than 0.70 (or about 0.70) Pascals and a phase angle δ of from about 40° to about 65° as measured by the Bohlin CVOR Rheometer Visco-Elastic Property Test Method.

11. The composition of claim 1, wherein the composition has:
   i. a surface tension ranging from about 40.8 dynes/cm to 51.9 dynes/cm as measured by the Rame-Hart—DROPimage Advanced Software Pendant Drop Method;
   ii. a rate of moisture loss of less than 1 mg/3 minutes at 37° C. and 70% relative humidity as measured by the DVS Intrinsic Measurement System and DVS-Intrinsic Control Software Method;
   iii. an elastic modulus G' greater than 0.70 (or about 0.70) Pascals and a phase angle δ of from about 40° to about 65° as measured by the Bohlin CVOR Rheometer Visco-Elastic Property Test Method.

* * * * *